(12) United States Patent
Yang

(10) Patent No.: US 7,261,687 B2
(45) Date of Patent: Aug. 28, 2007

(54) FORWARD SCANNING IMAGING OPTICAL FIBER PROBE

(75) Inventor: Changhuei Yang, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 187 days.

(21) Appl. No.: 11/087,396

(22) Filed: Mar. 22, 2005

(65) Prior Publication Data

US 2005/0234345 A1    Oct. 20, 2005

Related U.S. Application Data

(60) Provisional application No. 60/555,628, filed on Mar. 23, 2004.

(51) Int. Cl.
*A61B 1/07* (2006.01)
*G01J 3/45* (2006.01)

(52) U.S. Cl. ............ 600/173; 600/182; 600/176; 385/119; 356/455; 359/837

(58) Field of Classification Search ........... 600/182, 600/173, 176, 137, 473, 478; 385/116, 117, 385/119; 359/837; 356/455
See application file for complete search history.

(56) References Cited

U.S. PATENT DOCUMENTS 3,229,577 A * 1/1966 Ellinger .................... 359/367
4,717,823 A * 1/1988 Steimel et al. ............. 250/236
4,824,205 A * 4/1989 Yamashita et al. ......... 385/104
5,133,035 A * 7/1992 Hicks ........................ 385/117
5,425,123 A * 6/1995 Hicks ........................ 385/117
6,485,413 B1 * 11/2002 Boppart et al. ............ 600/160
6,626,828 B2 * 9/2003 Dohi et al. ................. 600/173
6,636,664 B2 * 10/2003 Snyder et al. .............. 385/36

* cited by examiner

*Primary Examiner*—John P Leubecker
(74) *Attorney, Agent, or Firm*—Townsend and Townsend and Crew LLP; Gerald T. Gray

(57) ABSTRACT

Probes, and systems and methods for optically scanning a conical volume in front of a probe, for use with an imaging modality, such as Optical Coherence Tomography (OCT). A probe includes an optical fiber having a proximal end and a distal end and defining an axis, with the proximal end of the optical fiber being proximate a light source, and the distal end having a first angled surface. A refractive lens element is positioned proximate the distal end of the optical fiber. The lens element and the fiber end are both configured to separately rotate about the axis so as to image a conical scan volume when light is provided by the source. Reflected light from a sample under investigation is collected by the fiber and analyzed by an imaging system. Such probes may be very compact, e.g., having a diameter 1 mm or less, and are advantageous for use in minimally invasive surgical procedures.

20 Claims, 2 Drawing Sheets

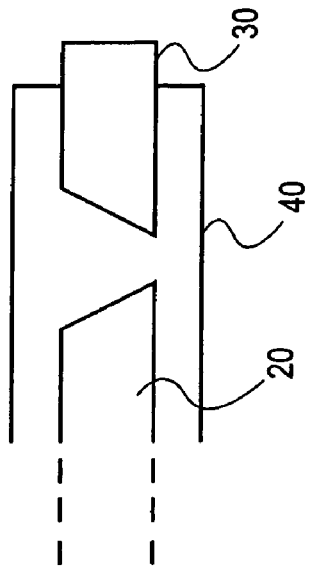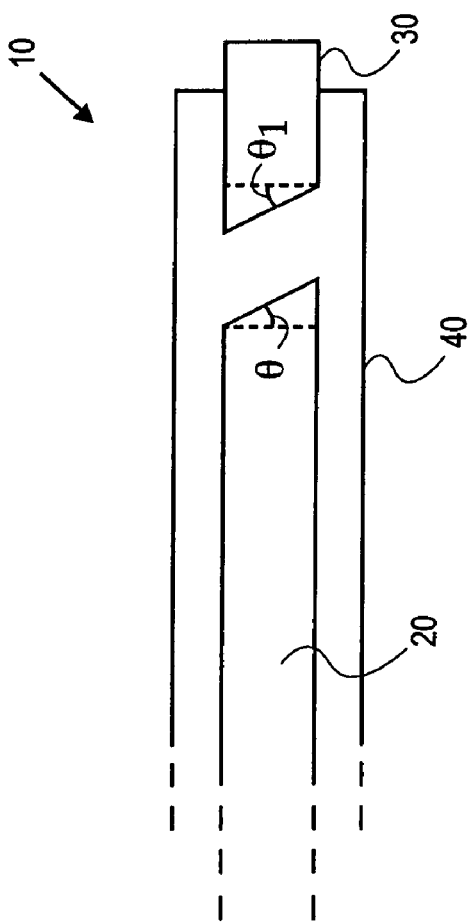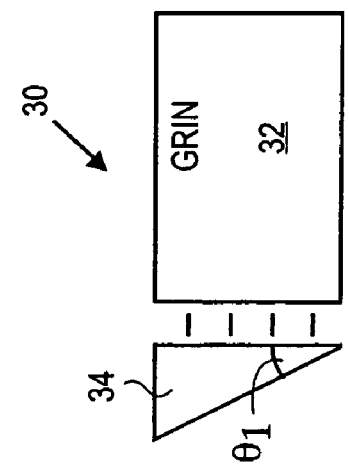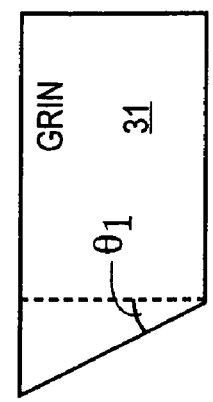
FIG. 4
FIG. 3
FIG. 1
FIG. 2

FORWARD SCANNING IMAGING OPTICAL FIBER PROBE

CROSS-REFERENCES TO RELATED APPLICATIONS

This application claims the benefit of U.S. Provisional Application No. 60/555,628 filed Mar. 23, 2004, the disclosure of which is incorporated herein by reference in its entirety.

BACKGROUND OF THE INVENTION

The present invention relates generally to optical probes and more particularly to optical probes for use with Optical Coherence Tomography (OCT) and other optical imaging modalities.

OCT is a laser based imaging modality that uses near infrared or infrared laser light to non-destructively image subsurface tissue structures. An imaging depth on the order of millimeters (mm), with a spatial resolution of a few micrometers ($\mu$m) is relatively easily achieved using OCT at practical light fluence levels on the order of 100 $\mu$W. OCT is therefore very useful for in vitro and in vivo tissue structure imaging applications such as may be used during minimally invasive surgical procedures. Currently, both side-imaging endoscope systems and forward imaging endoscope systems are known.

The construction of a needle endoscope that is capable of performing forward OCT imaging presents very significant design challenges. Current endoscopes are typically more than 5 mm thick. The thickness of such probes, especially when compared with their en face imaging area, e.g., about 2 mm wide, makes them undesirable as a needle endoscope for image-guided surgical procedures. One major challenge of making a thin endoscope lies with the difficulty of designing a probe beam deflection system that is capable of covering a sufficient scan volume while constraining the probe diameter to be less than about 2 mm to minimize the invasiveness of the probe. A reasonable OCT scan volume for providing sufficient image information would be a conical volume that is about 3 mm in length and about 2 mm in diameter at its maximum circumference.

Therefore it is desirable to provide probes such as forward imaging endoscope needles useful for OCT imaging of a scan volume that overcome the above and other problems.

BRIEF SUMMARY OF THE INVENTION

The present invention provides forward imaging optical endoscope probes useful in imaging applications, and in particular in imaging applications using OCT as the imaging modality. The endoscope probes of the present invention advantageously allow for improved high-resolution imaging of non-transparent tissue structures in the immediate vicinity of the endoscope needle tip.

According to the present invention, a probe includes an optical fiber having a proximal end and a distal end and defining an axis, with the proximal end of the optical fiber being proximate a light source, and the distal end having a first angled surface. A refractive lens element is positioned proximate the distal end of the optical fiber. The lens element and the angled fiber end are both configured to separately rotate about the axis so as to image a conical scan volume when light is provided by the source. Reflected light from a sample under investigation is collected by the fiber and analyzed by an imaging system. Such probes may be very compact, e.g., having a diameter 1 mm or less, and are advantageous for use in minimally invasive surgical procedures.

According to one aspect of the present invention, an optical apparatus is provided that typically includes an optical fiber including a proximal end and a distal end and defining an axis, wherein the proximal end of the optical fiber is proximate a light source, and wherein the distal end comprises a first angled surface. The apparatus also typically includes a refractive lens element proximate the distal end of the optical fiber, wherein the lens element and the optical fiber are both configured to rotate about the axis, and wherein the optical fiber and the lens are configured to rotate relative to each other about the axis.

According to another aspect of the present invention, an optical apparatus is provided that typically includes an optical fiber having a proximal end and a distal end and defining an axis, wherein the proximal end of the optical fiber is proximate a light source, and wherein the distal end is proximal a first refractive lens element. The apparatus also typically includes a second refractive lens element proximate the first lens element, wherein the second lens element is configured to rotate about the axis, and wherein the first lens element is configured to rotate about the axis separate from the second lens element.

According to yet another aspect of the present invention, a method is provided for imaging a forward scan volume of a tissue sample using a forward scanning probe that typically includes an optical fiber including a proximal end and a distal end and defining an axis, wherein the proximal end of the optical fiber is proximate a light source, and wherein the distal end is proximal a first refractive lens element. The probe further typically includes an imaging end having a second refractive lens element positioned proximate the first lens element, wherein the second lens element is configured to rotate about the axis, and wherein the first lens element is configured to rotate about the axis separate from the second lens element. The method typically includes positioning the imaging end of the probe proximal a tissue sample to be imaged, providing a light beam to the proximal fiber end from the light source, rotating the inner tube at a first rate, and simultaneously rotating the outer tube at a second rate different from the first rate so as to image a conical scan volume of the tissue sample.

Reference to the remaining portions of the specification, including the drawings and claims, will realize other features and advantages of the present invention. Further features and advantages of the present invention, as well as the structure and operation of various embodiments of the present invention, are described in detail below with respect to the accompanying drawings. In the drawings, like reference numbers indicate identical or functionally similar elements.

BRIEF DESCRIPTION OF THE DRAWINGS

FIG. 1 illustrates a side view of a probe design including a fiber and a lens element according to one embodiment.

FIG. 2 illustrates a side view of a lens element design according to one embodiment.

FIG. 3 illustrates another embodiment of a lens element design.

FIG. 4 illustrates an orientation of the elements of FIG. 1 that results in a maximum angle of the forward light beam with respect to the forward axis.

DETAILED DESCRIPTION OF THE INVENTION

Figure 5A:
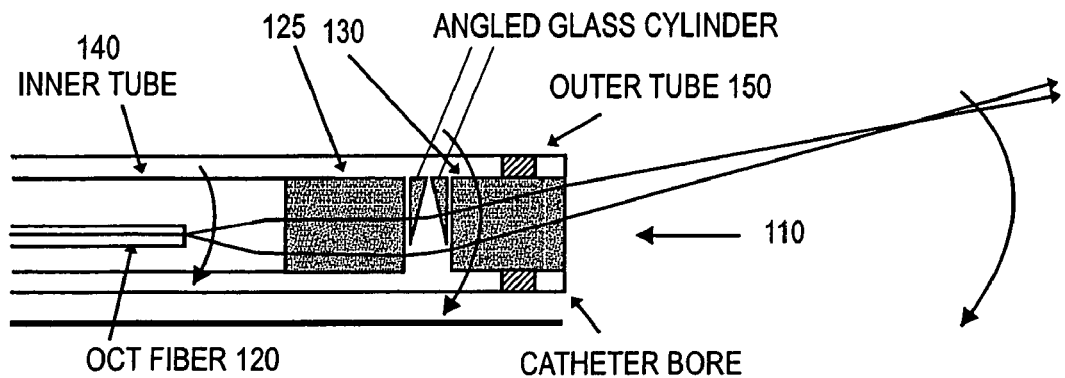
FIG. 5a illustrates a side view of a probe design according to another embodiment of the present invention.

The present invention provides novel probes, and systems and methods for optically scanning a conical volume in front of a probe, for use with an imaging modality, such as Optical Coherence Tomography (OCT). Other useful imaging modalities for which probes of the present invention are useful include Optical Doppler Tomography (ODT), and Speckle Decorrelation Tomography (SDT).

A probe 10 according to one embodiment is shown in FIG. 1. As shown, probe 10 includes an optical fiber 20 and a lens element 30 proximal the end of fiber 20. A tube 40 encloses fiber 20. Tube 40 is also coupled to lens element 30 to facilitate rotation of lens element 30 relative to fiber 20. Fiber 20 may itself be rotated separately from tube 40, in one aspect, as will be described in more detail below with reference to FIG. 5.

In one aspect, fiber 20 includes a single mode fiber (although multimode fibers can be used if desired) having an end that is angled cut at an angle of θ as shown in FIG. 1. Input light from a light source (not shown) positioned proximal a distal end of fiber 20 enters fiber 20 and exits at the end of fiber 20 proximal lens element 30. The light exiting from the fiber 20 will be incident on focusing lens element 30. In one aspect, it is preferred that the light source provides collimated light in the infrared (IR) or near-IR wavelength range. Of course, other wavelengths may be used as desired. One example of a useful light source is a laser or a diode laser that emits in the IR or near-IR wavelength range. FIGS. 2 and 3 show examples of two possible ways the focusing lens element 30 may be constructed.

According to one embodiment, as shown in FIG. 2, lens element 30 includes a (cylindrical) GRIN lens 31 that is cut and polished at one end to have an angle of $\theta_1$. The angle $\theta_1$ is chosen so that when the GRIN lens 31 and the end of fiber 20 are oriented in the manner shown in FIG. 1, the exiting light beam from the GRIN lens 31 is focused in the forward direction. In one aspect, therefore, the angle $\theta_1$ should be substantially close (e.g., within 1° or 2°) to θ, the angle at the fiber end.

According to another embodiment, as shown in FIG. 3, lens element 30 includes a (cylindrical) GRIN lens 32 and an angled glass wedge element 34 attached to the GRIN lens 32. Wedge element 34 is preferably formed (e.g., cut and polished) from a cylindrical glass element. Wedge element 34 may be glued or otherwise secured to GRIN lens 32. The choice of angle cut presented by the wedge 34 is determined by the same considerations as described above. For example, the angle $\theta_1$ should be substantially close (e.g., within 1° or 2°) to θ, the angle at the fiber end.

In one aspect, rotation of the GRIN lens element 30 shown in FIG. 2 (or the GRIN-wedge construction shown in FIG. 3) with respect to a fixed fiber orientation will vary the angle of the forward light beam from zero degrees to a certain angle with respect to the forward axis. Zero angle is achieved when the two elements are oriented as shown in FIG. 1. The maximum angle is achieved when the two elements are oriented as shown in FIG. 4. A visualization of the zero angle and maximum angle can be seen in FIG. 5b and 5a, respectively, which illustrate a slightly different probe configuration. The continuous rotation of the lens element 30 between those two orientations will complete a span of the angle between the zero angle and maximum angle values. Therefore, in one aspect, rotation of both elements will allow for a conical scan volume to be imaged. For example, rotating the fiber 20 at one rate and the GRIN lens 30 of FIG. 2 (or GRIN-wedge construction of FIG. 3) at a different rate allows for a forward conical scan volume to be taken.

The focal length of the lens element 30 and the distance from the tip of fiber 20 is preferably selected so that the output light forms a focus at an appropriate desired distance in the foreground. For example, in an OCT imaging system, the focal point can be chosen to be at half the penetration depth of the OCT imaging capability. A useful focus length for many applications is about 2.0 mm, however, it should be understood that a focal length of between about 0.1 mm and about 10 mm or more can be implemented.

FIG. 5 illustrates a probe 110, and a probe scan system, according to another embodiment of the present invention. In the embodiment shown, optical probe 110 includes a pair of GRIN lenses and a pair of cylindrical glass elements that are cut at an appropriate angle θ. As shown, probe 110 includes an optical fiber 120 and a fiber lens element 125 proximal the end of fiber 120. A first tube 140 ("inner tube") encloses fiber 120. Inner tube 140 is also coupled to fiber lens element 125 to facilitate rotation of lens element 125. A second rotatable tube 150 ("outer tube") encloses tube 140 and refractive lens element 130 to facilitate rotation of lens element 130 relative to fiber lens element 125. Input light from a light source (not shown) at a distal end of fiber 120 enters fiber 120 and exits the fiber end internal to inner tube 140 as shown. In one aspect, the optical fiber 120 is fixed at the focal point of fiber lens element 125 within the inner tube. In preferred aspects, lens element 125 includes a GRIN lens. The GRIN lens may be cut at an angle or it may be coupled with an angled wedge element (e.g., similar to wedge 34 discussed above with reference to FIG. 3) as shown. In this case, the light output is collimated by the GRIN lens and angularly displaced by the angled glass wedge element. The tilted beam is brought to a focus by lens element 130, which in one aspect as shown includes a second glass wedge element and GRIN lens pair, and which is attached to the outer tube.

Figure 5B:
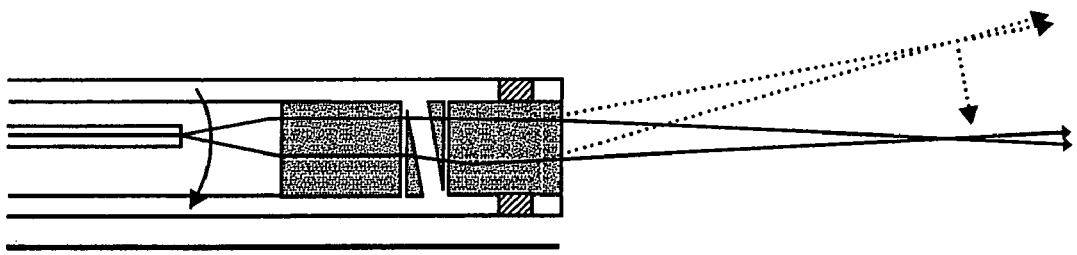
FIG. 5b illustrates an orientation of the elements of FIG. 5a that results in a zero angle of the forward light beam with respect to the forward axis.

The rotation of lens element 130 with respect to fiber lens element 125 will change the angle of the forward light beam with respect to the forward axis. For example, FIG. 5a shows the orientations that provide a maximum angle, and FIG. 5b show the orientations that provide a zero angle. If the angular difference between the orientation of the first and second angled surfaces is given by $\Delta\phi$ ($\Delta\phi=0$ when the cylinders are oriented as shown in FIG. 5b), the angle made by the output beam to the forward axis is approximately given by:

$$\psi \approx \theta\sqrt{(n-1)^2(1-\cos(\Delta\phi)^2)+\sin(\Delta\phi)^2} \tag{6}$$

where n is the refractive index of the cylinders. By rotating fiber lens element 125 with respect to lens element 130, the angle ψ made by the output beam relative to the forward axis can be changed from 0 to 2(n−1) rads. Rotating both lens elements in synchrony scans the output beam in a complete circular cone. If the focal point of the output is 2 mm from the probe tip and it is desirable to cover a scan area 2 mm in diameter at that distance, the angular cut, θ, should be about 0.19 rads (about 11°). Given the smallness of the angle, in one aspect, the design is further simplified by simply cutting the GRIN lenses with the given angular tilt, eliminating the need for glass wedge elements.

Figure 5C:
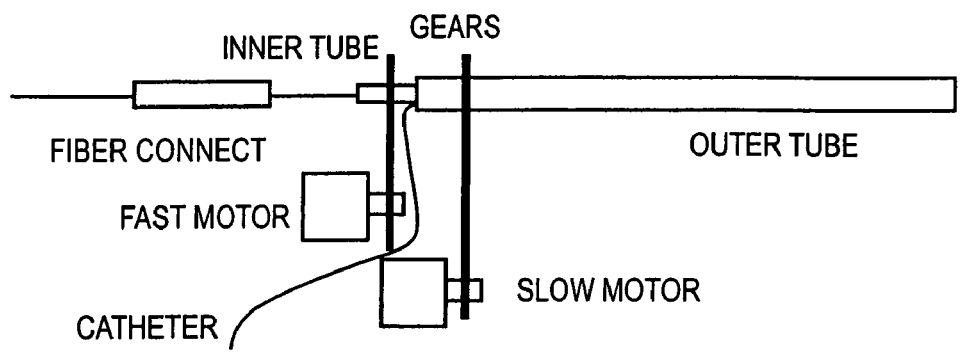
FIG. 5c illustrates a rotation actuation system according to one embodiment.

In one embodiment, the outer and inner tubes (holding lens element 130 and fiber 120, respectively) are preferably mounted to two different motors via gears as shown in FIG. 5c. In the embodiment of FIG. 1, tube 40 and fiber 20 may similarly be coupled to different motors. In both cases, the complete rotation of the refractive lens element and the fiber end with respect to a reference plane will complete a conical sweep. Therefore, the combination of these two motions will create a scan volume equal to a solid cone with a maximum angle from the forward axis given by the considerations described above. Each motor preferable provides one or multiple rotational speeds in the range of a fraction of a HZ to about 1 KHz or more. Also, each motor may rotate the coupled elements in the same or opposite direction as the other motor. Further, the fiber 120 need not rotate with the fiber lens element 125; that is inner tube may rotate without rotation of fiber 120. It should also be appreciated that a single motor may be used to rotate both the inner and outer tubes. In this case, a ratchet and pawl type mechanism coupling the motor to both tubes may be used to rotate the tubes at different rotational speeds. Examples of a similar rotation actuation system and a fiber connection to an OCT imaging system for a side scanning probe is shown in "Scanning single-mode fiber optic catheter-endoscope for optical coherence tomography", Optics Letters, V21, pg. 543 (1996), which is hereby incorporated by reference.

By using OCT imaging to create depth resolved imaging along each light beam path orientation, a three dimensional image of the structure in front of the imaging needle (probe) can be constructed. For example, an imaging Fourier Domain OCT (FDOCT) engine can be used with the probes of the present invention to acquire tomographic images of the forward scan volume. Given the large forward scan volumes possible (e.g., about 3-4 mm forward and an area of diameter 4 mm at the 4 mm forward distance point), a needle endoscope according to the present invention provides unprecedented forward imaging capability. For example, by rotating the inner tube at 100 Hz and the outer tube at 1 Hz, a 3 dimensional image with a total of $10^8$ voxel per second can be generated with an OCT imaging system that is capable of acquiring 100 kHz rate A-scans with 1,000 pixels each.

This innovative and yet elegantly simple design enables very compact probes to be built, e.g., probes of diameter 1 mm or less (e.g., 500 microns or less). Such devices provide a dramatic improvement over existing endoscopic imaging technology. The compact size and forward tomographic imaging capability of the probes of the present invention make image guidance of minimally invasive surgical procedure possible.

While the invention has been described by way of example and in terms of the specific embodiments, it is to be understood that the invention is not limited to the disclosed embodiments. To the contrary, it is intended to cover various modifications and similar arrangements as would be apparent to those skilled in the art. For example, rather than having a flat end face, a GRIN lens may be angled cut and a wedge element may be attached thereto and cut so as to provide the desired angled surface, e.g., $\theta$ or $\theta_1$. Additionally, the tubes holding the lens elements and fibers may comprise a flexible or rigid material. Therefore, the scope of the appended claims should be accorded the broadest interpretation so as to encompass all such modifications and similar arrangements.

What is claimed is:

1. An optical apparatus, comprising:
   an optical fiber including a proximal end and a distal end and defining an axis, wherein the proximal end of the optical fiber is proximate a light source, and wherein the distal end comprises a first angled surface; and
   a refractive lens element proximate the distal end of the optical fiber, wherein the lens element and the optical fiber are both configured to rotate about said axis, and wherein the optical fiber and the lens are configured to rotate relative to each other about said axis;
   a motor adapted to cause the optical fiber to rotate about said axis; and
   a coupling mechanism that couples the motor to the lens element such that the motor also causes the lens element to rotate about said axis, wherein the coupling mechanism is adapted to rotate the lens element about said axis at a different rate than a rate of rotation of the optical fiber about said axis.

2. The optical apparatus of claim 1, wherein the lens element includes a second angled surface that is substantially complementary to the first angled surface of the optical fiber when the lens element is in a first rotational orientation about said axis.

3. The optical apparatus of claim 1, wherein the lens element includes a GRIN lens.

4. The optical apparatus of claim 3, wherein the lens element includes an optical wedge element attached to an end face of the GRIN lens.

5. The optical apparatus of claim 1, wherein the coupling mechanism includes a ratchet and pawl type coupler.

6. The optical apparatus of claim 1, wherein the optical apparatus is an optical coherence microscope probe.

7. The apparatus of claim 1, wherein the distal end of the fiber includes a GRIN lens that is angled cut at an angle relative to a plane normal to said axis.

8. The apparatus of claim 1, wherein the distal end of the fiber includes a GRIN lens and an optical wedge element attached to an end face of the GRIN lens.

9. An optical apparatus, comprising:
   an optical fiber including a proximal end and a distal end and defining an axis, wherein the proximal end of the optical fiber is proximate a light source, and wherein the distal end is proximal a first refractive lens element; and
   a second refractive lens element proximate the first lens element, wherein the second lens element is configured to rotate about said axis, and wherein the first lens element is configured to rotate about said axis separate from the second lens element, and wherein the first lens element rotates at a different rate of rotation than a rate of rotation of the second lens element.

10. The apparatus of claim 9, wherein the first lens element includes a GRIN lens that is angled cut at a first angle relative to a plane normal to said axis.

11. The apparatus of claim 10, wherein the second lens element includes a second GRIN lens that is angled cut at a second angle relative to the plane normal to said axis, said second angle being substantially the same as the first angle.

12. The apparatus of claim 10, wherein the second lens element includes a second GRIN lens and a second optical wedge element attached thereto, said second wedge element providing an end face at a second angle relative to a plane normal to said axis, said second angle being substantially the same as the first angle.

13. The apparatus of claim 9, wherein the first lens element includes a GRIN lens and an optical wedge element attached thereto, said wedge element providing an end face at a first angle relative to a plane normal to said axis.

14. The apparatus of claim 9, comprising a first motor coupled with the fiber, and a second motor coupled with the second lens element, wherein the first motor is configured to rotate the first lens element about said axis, and wherein the second motor is configured to rotate the second lens element about said axis in a different or same rotational direction as the first lens element.

15. A method of imaging a forward scan volume of a tissue sample using a forward scanning probe that includes an optical fiber including a proximal end and a distal end and defining an axis, wherein the proximal end of the optical fiber is proximate a light source, and wherein the distal end is proximal a first refractive lens element, wherein the probe further includes an imaging end having a second refractive lens element positioned proximate the first lens element, wherein the second lens element is configured to rotate about the axis, and wherein the first lens element is configured to rotate about the axis separate from the second lens element, the method comprising:
    positioning the imaging end of the probe proximal a tissue sample to be imaged;
    providing a light beam to the proximal fiber end from the light source;
    rotating the first lens element at a first rate; and
    simultaneously rotating the second lens element at a second rate different from the first rate.

16. The method of claim 15, wherein light reflected by the tissue sample is collected in the fiber, the method further comprising capturing the reflected light from the tissue sample in the fiber using an optical coherence tomography imaging system.

17. The method of claim 15, wherein the light beam has a wavelength in one of the IR or near-JR wavelength spectrum.

18. The method of claim 15, wherein each of the first lens element and second lens element is rotated at between approximately 1 Hz and approximately 1 kHz.

19. The method of claim 18, wherein the first lens element is rotated at approximately 100 Hz and wherein the second lens element is rotated at approximately 1 Hz.

20. An optical apparatus, comprising:
    an optical fiber including a proximal end and a distal end and defining an axis, wherein the proximal end of the optical fiber is proximate a light source, and wherein the distal end comprises a first angled surface; and
    a refractive lens element proximate the distal end of the optical fiber, wherein the lens element and the optical fiber are both configured to rotate about said axis, and wherein the optical fiber and the lens are configured to rotate relative to each other about said axis;
    a first motor adapted to cause the optical fiber to rotate about said axis; and
    a second motor adapted to cause the lens element to rotate about said axis in a different or same rotational direction as the optical fiber,
    wherein the second motor rotates the lens element about said axis at a different rate than a rate of rotation of the optical fiber about said axis.

* * * * *